(12) United States Patent
Yang et al.

(10) Patent No.: US 7,682,826 B2
(45) Date of Patent: Mar. 23, 2010

(54) HUMAN EMBRYONIC STEM CELLS AND CULTURING METHODS THEREOF

(75) Inventors: Mei Ju Yang, Hsinchu (TW); Kuang Ning Chang, Taoyuan County (TW); Lih Tao Hsu, Taoyuan County (TW); Jun Jae Huang, Miaoli County (TW); Wann Hsin Chen, Hsinchu (TW); Chao Ying Kuo, Hsinchu (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 737 days.

(21) Appl. No.: 11/233,055

(22) Filed: Sep. 23, 2005

(65) Prior Publication Data

US 2006/0030040 A1  Feb. 9, 2006

Related U.S. Application Data

(63) Continuation-in-part of application No. 10/839,212, filed on May 6, 2004, now abandoned.

(30) Foreign Application Priority Data

Dec. 9, 2003  (TW) .............................. 92134707 A

(51) Int. Cl.
*C12N 5/00* (2006.01)
(52) U.S. Cl. ..................... 435/377; 435/325; 435/375
(58) Field of Classification Search ........................ None
See application file for complete search history.

(56) References Cited

U.S. PATENT DOCUMENTS

| | | | |
|---|---|---|---|
| 4,816,561 A | 3/1989 | Todaro | 530/324 |
| 5,453,357 A | 9/1995 | Hogan | 435/7.21 |
| 5,690,926 A | 11/1997 | Hogan | 424/93.1 |
| 5,843,780 A | 12/1998 | Thomson | 435/363 |
| 6,458,589 B1 | 10/2002 | Rambhatla et al. | |
| 6,800,480 B1 | 10/2004 | Bodnar et al. | 435/325 |
| 2002/0022268 A1 | 2/2002 | Xu et al. | |
| 2003/0017589 A1 | 1/2003 | Mandalam et al. | 435/366 |
| 2003/0143736 A1 | 7/2003 | Bongso et al. | |
| 2003/0175956 A1 | 9/2003 | Bodnar et al. | |

FOREIGN PATENT DOCUMENTS

| | | | |
|---|---|---|---|
| WO | WO 99/20741 | * | 4/1999 |
| WO | 03/014313 | | 2/2003 |
| WO | 03/020920 | | 3/2003 |
| WO | WO 03/020920 | | 3/2003 |
| WO | 03/002944 | | 10/2003 |

OTHER PUBLICATIONS

Kaighn ME et al. 1981. Growth control of prostatic carcinoma cells in serum-free media: interrelationship of hormone response, cell density, and nutrient media. Proc Natl Acad Sci USA 78: 5673-5676.*
Scott RW et al. 1983. Purification of human protease nexin. J Biol Chem 258: 10439-10444.*
Outi Hovatta et al, "A culture system using human foreskin fibroblasts as feeder cells allows production of human embryonic stem cells", Human Reproduction, vol. 18, No. 7, pp. 1404-1409, 2003.
Benjamin E. Reubinoff et al., "Embryonic stem cell lines from human blastocysts: somatic differentiation in vitro", Nature Biotechnology, vol. 18, pp. 399-404, Apr. 2000.
James A. Thomson et al., "Embryonic Stem Cell Lines Derived from Human Blastocysts", Science, vol. 282, pp. 1145-1147, Nov. 6, 1998.
Jong Hyuk Park et al., "Establishment and Maintenance of Human Embryonic Stem Cells on STO, a Permanently Growing Cell Line", Biology of Reproduction 69, 2007-2014, 2003.
Andre B. H. Choo et al., "Expansion of Pluripotent Human Embryonic Stem Cells on Human Feeders", Biotechnology and Bioengineering, vol. 88, No. 3, pp. 321-331, Nov. 5, 2004.
M. Amit et al., "Feeder Layer- and Serum-Free Culture of Human Embryonic Stem Cells", Biology of Reproduction 70, 837-845, 2004.
Chunhui Xu et al., "Feeder-free growth of undifferentiated human embryonic stem cells", Nature Biotechnology, vol. 19, pp. 971-974, Oct. 2001.
Linzhao Cheng et al., "Human Adult Marrow Cells Support Prolonged Expansion of Human Embryonic Stem Cells in Culture", Stem Cells, 2003; 21:131-142.
M. Amit et al., "Human Feeder Layers for Human Embryonic Stem Cells", Biology of Reproduction 68, 2150-2156, 2003.
M. Jordana et al., "Immune-inflammatory functions of fibroblasts", Eur Respir J, 1994, 7, 2212-2222, Series 'Pulmonary Immune Cells'.
Mark Richards et al., "Human feeders support prolonged undifferentiated growth of human inner cell masses and embryonic stem cells", Nature Biotechnology, vol. 20, pp. 933-936, Sep. 2002.

* cited by examiner

*Primary Examiner*—Lora E Barnhart
(74) *Attorney, Agent, or Firm*—Bacon & Thomas, PLLC

(57) ABSTRACT

Provided herein are human embryonic stem cells and their method of culturing. In one embodiment, the human embryonic stem cells are maintained in an environment containing an extracellular matrix isolated from feeder cells and a conditioned medium pre-conditioned by the feeder cells; the feeder cells are pre-inactivated by either gamma ray radiation or by mitomycin C treatment. The cultured human embryonic stem cells remain substantially undifferentiated and maintain their pluripotency to differentiate into three germ layer cells.

1 Claim, 15 Drawing Sheets

HUMAN EMBRYONIC STEM CELLS AND CULTURING METHODS THEREOF

RELATED APPLICATIONS

This application is a continuation-in-part of application Ser. No. 10/839,212, filed on May 6, 2004, now abandoned.

FIELD OF THE INVENTION

The present invention relates to human embyronic stem (HES) cells and to methods for culturing such cells. More particularly, the present invention provides methods for culturing HES cells in a substantially undifferentiated state without a layer of feeder cells.

BACKGROUND OF THE INVENTION

Embryonic stem cells are pluripotent stem cells derived from the inner cell mass of embryo in blastocyst phase. They can be induced to differentiate into all three germ layer cells and have great potential for clinical applications including drug development, cell sources for tissue engineering and cell therapy. However most of human embryonic stem (HES) cells are cultured in the presence of either mouse embryonic fibroblasts (MEF) or human cells nowadays. Thomson et al. (U.S. Pat. No. 5,843,780) were the first to successfully culture stem cells from primates and human. They cultured HES cells on a layer of feeder cells, which were mouse embryonic fibroblasts that serve as an adherent layer for the stem cells and as a source of nutrients, bioactive material, and growth factors.

Nowadays, most of HES cells are maintained in culture in an undifferentiated state on a layer of inactivated feeder cells originated from either mouse or human. Some problems exist in a feeder layer dependent culture system for manipulation and clinical application of HES cells, for example, (1) the potential risks of transmitting pathogens from the animal feeder cells to the HES cells during cell therapy, (2) feeder cells are mainly from primary cells, while primary cells from different batches offer different effect as feeder cells, rendering the quality control of the cultured HES cells more difficult; (3) the limited sources and numbers of feeder cells hamper the mass production and applications of HES cells. Therefore, it is desirable to maintain the undifferentiated growth of HES cells without using the feeder cells for mass production and clinical application of HES cells.

Xu et al (Nat. Biotechnol., 19(10):971-974, 2001; WO 03/020920 and U.S. 2003/0017589) were the first to successfully maintain undifferentiated growth of HES cells in a feeder-free culture system. In this system, HES cells are cultured on Matrigel® or laminin in a medium pre-conditioned by mouse embryonic fibroblasts (MEF). Matrigel is a solubulized basement membrane preparation extracted from mouse sarcoma, a tumor rich in extracellular matrix (ECM) proteins. It has the potential risk of transmitting xeno agents during clinical applications of HES cells. Furthermore, such matrices and defined-matrix macro-molecules as of Matrigel are insufficient in mimicking the more complex cell-martix interactions provided by the feeder cells. Another study has also indicated that this culture system is only suitable for certain HES cell lines, e.g. H1 and H9, but unsuitable for other HES cell lines (Richards, M. et al., Nat Biotechnol., 20(9):933-936, 2002).

Accordingly, it is an object of the present invention to provide an alternative feeder-free culture system to overcome the afro-mentioned problems encountered in the prior art such as potential pathogen transmitting during cell therapy, poor quality control and etc., and to grow substantially undifferentiated HES cells for periods sufficient to allow the production of HES cells for applications such as cell therapy, drug discovery and gene therapy.

SUMMARY

The present invention provides HES cells and methods of culturing such cells. One aspect of the invention provides a method of proliferating HES cells comprising: culturing the HES cells in an environment containing ECM isolated from feeder cells and a conditioned medium pre-conditioned by the feeder cells, wherein the feeder cells are pre-inactivated by gamma ray irradiation or by treatment with mitomycin C. In some embodiments, at least 60% of the HES cells remain pluripotent and substantially undifferentiated when proliferated by the method of this invention. In one preferred embodiment, HES cells proliferated by the method of this invention are pluripotent and at least 78% of the HES cells remain substantially undifferentiated after 5 passages.

A further aspect of the present invention provides a system for maintaining undifferentiated growth of HES cells, comprising: a substrate covered with ECM isolated from feeder cells; a conditioned medium that was pre-conditioned by the feeder cells; and undifferentiated human embryonic stem cells; wherein the feeder cells are pre-inactivated by gamma ray irradiation or by treatment with mitomycin C. In one embodiment, at least 78% of the HES cells proliferated by the system of this invention remained substantially undifferentiated for at least 5 passages.

Another aspect of the invention provides an isolated population of pluripotent HES cells. Another aspect of the invention provides cryopreserved HES cells obtained from the method of this invention.

These and other aspects and advantages will become apparent when the Description is read in conjunction with the accompanying Examples. It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1A:
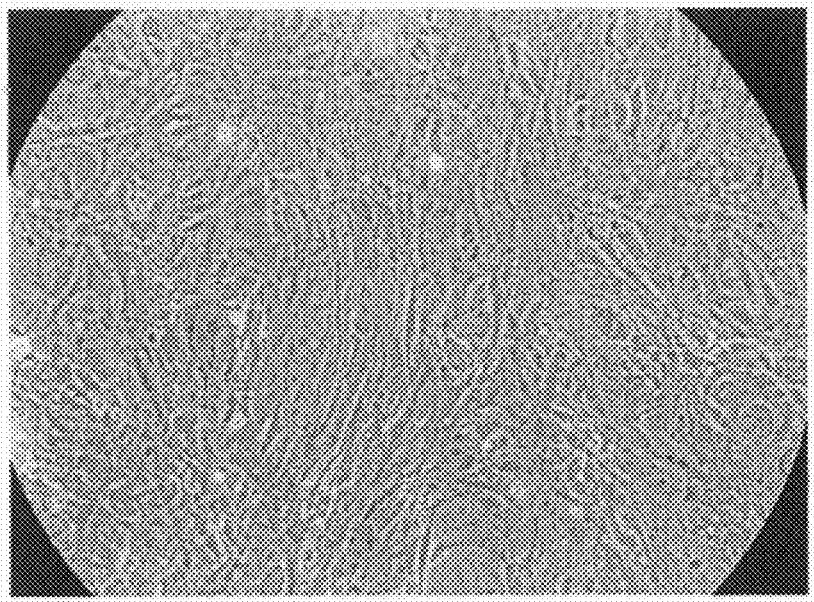
FIGS. 1A and 1B are phase-contrast photographs of primary mouse embryonic fibroblast (PMEF) and ECM derived from PMEF, respectively, when viewed under a light transmitted microscope (300×)

The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

As used herein, the term "pluripotent stem cell" refers to a cell that has the ability to self replicate for indefinite periods and can give rise to may cell types under the right conditions, particularly, the cell types that derived from all three embryonic germ layers—mesoderm, endoderm, and ectoderm.

As used herein, the term "feeder cells" refers to cells of one tissue type that are co-cultured with cells of another tissue type, to provide an environment in which cells of the second tissue type may grow. The feeder cells are optionally from a different species as the cells they are supporting. For example, HES cells of this invention can be supported by primary cultures of mouse embryonic fibroblasts, or human fibroblasts as described later in this disclosure. Feeder cells are usually adherent growth-arrested but viable and bioactive cells (primary cells or immortalized cell lines) that have been inactivated, for example, by gamma ray irradiation or by treatment with mitomycin C, to limit replication.

As used herein, the term "ECM" refers to a particulate a cellular matrix composed of extracellular and cellular matrices isolated from feeder cells. In one preferred embodiment, the feeder cells are human foreskin fibroblasts (HFF). In another preferred embodiment, the feeder cells are primary mouse embryonic fibroblasts (PMEF), however, other types of fibroblasts may also be used.

As used herein, the term "conditioned medium" refers to a medium harvested after the feeder cells have been cultivated within for a period of time. The conditioned medium of the present invention may then be used to cultivate HES cells, for it contains many mediator substances, such as growth factors and cytokines, that were secreted by the feeder cells cultivated previously and can thus help promote the growth of HES cells. In one embodiment, the conditioned medium is a medium harvested after the feeder cells have been cultivated in it for at least 1 day.

All other acronyms and abbreviations have the corresponding meaning as published in journals related to the arts of chemistry and biology.

The present invention provides a method of proliferating HES cells in a feeder-free system, which mainly composed of a substrate covered with ECM isolated from feeder cells pre-inactivated by gamma ray irradiation or by treatment with mitomycin C and a conditioned medium pre-conditioned by the feeder cells. We discovered that with the combinational use of ECM prepared by one embodiment of this invention and a condition medium, the undifferentiated growth of HES cells is significantly enhanced. Moreover, the efficacy of ECM prepared in accordance with the method of this invention in sustaining the undifferentiated growth of HES cells is far more better than ECM prepared by the conventional method, i.e., the method according to U.S. Pat. No. 6,800,480.

Suitable feeder cells that may be used for this invention include, but not limited to, a human foreskin fibroblast (HFF), a primary mouse embryonic fibroblast (PMEF), a mouse embryonic fibroblast cell line (MEF), a murine fetal fibroblast (MFF), a human embryonic fibroblast (HEF), a human fetal muscle cell (HFM), a human fetal skin cell (HFS), a human adult skin cell, a human adult fallopian tubal epithelial cell (HAFT) and a human marrow stromal cells (hMSCs) (See WO 03/02944; WO 03/014313; J. H. Park et al., Biol Reprod., 69:2007-2017, 2003; M. Amit et al., Biol Reprod., 68 (6): 2150-2156, 2003; Outi Hovattal et al., Hum. Reprod., 18 (7): 1404-1409, 2003; Richards, M. et al., Nat Biotechnol., 20(9): 933-936, 2002; James A. et al., Science, 282 (6):1145-1147, 1998; and Linzhao Cheng et al., Stem Cells, 21:131-142, 2003).

In general, the feeder cells were cultivated according to cultivation methods well known in this art. For general techniques in cell culture, please refer to standard textbooks and review articles in cell biology, such as "Animal Cell culture: A Manual of Basic Technique, R. I. Freshney, ed., 4th Edition, Wiley-Liss, Inc. 1987; and Hu et al., Curr. Opin. Biotechnol. 8(2):148-153, 1997. Once the feeder cells had reached confluence, they were treated with either gamma ray radiation or with mitomycin C to arrest the cell growth, so that the surviving cells lost the capability to proliferate, but retained their physiological functions, such as metabolism and synthesis of growth factors. The total dosage range of gamma ray radiation was between 3,000 rads to 6,000 rads, preferably greater than 5,000 rads. The suitable concentration of mitomycin C was between 1 μg/ml to 50 μg/ml, preferably between 5 μg/ml to 25 μg/ml. In one preferred embodiment, the inactivated feeder cells are primary human foreskin fibroblasts (HFF). In another preferred embodiment, the inactivated feeder cells are mouse embryonic fibroblasts (PMEF), however, other types of feeder cells may also be used.

For preparation of the conditioned medium, the gamma ray-and/or mitomycin C-inactivated feeder cells were re-cultivated in a growth medium for a period of at least 1 day, and the culture medium was then collected. The medium thus harvested was termed "condition medium", and was used in combination with ECM isolated according to the method of this invention, which will be described later in this disclosure, for sustaining and maintaining the undifferentiated growth of HES cells. The major ingredients of the conditioned medium are typically amino acids, vitamins, carbohydrates, inorganic ions, growth factors and some other bioactive substances.

The extracellular matrix (ECM) is not merely a passive structure. In the past few years, ECM has been identified as a dynamic action zone that functions to instruct cellular phenotype and physiological function. ECM proteins interact directly with cell surface receptors to initiate signal transduction pathways and to modulate those triggered by growth factors. ECM also controls the activity and presentation of a wide range of growth factors. Thus, modulation of the ECM, by remodeling its structure and activity, has profound effects on its function and the consequent behavior of cells residing on or within it. ECM may be prepared by methods known in the art. See e.g., Jordana et al. Eur. Respir. J. 7(12):2212-2222, 1994; and U.S. Pat. No. 4,816,561. In this invention, we found ECM isolated from cells that were grown or pretreated by different methods showed different supporting effects. In general, ECM was prepared by lysing the gamma ray-or mitomycin C-inactivated feeder cells, such as PMEF or HFF, with an alkali solution (e.g., NaOH) or trinitrotoluene (Triton), and followed by rinsing with sufficient amount of buffer solution, so that only the cytoskeleton and its associated proteins such as collagen, elastins, fibrillin, fibronectin, and laminin and glycans such as proteoglycans and glycosaminoglycans (GAGs) are preserved after washing. The ECM thus prepared was used as a scaffold for the stem cells of this invention to grown and/or proliferate on. Though undifferentiation ratio of HES cells cultured in accordance with the method of this invention varied from passage to passage, such as between about 60% to about 100%, however, in most of the cases, at least 60% of HES cells remained substantially undifferentiated. In one preferred example, at least 78% of HES cells cultured in accordance with the method of this invention remained pluripotent and undifferentiated after 5 passages, Example 3 of this invention further demonstrated that ECM prepared by the method of this invention is far superior in supporting undifferentiated growth of HES cells than ECM prepared by the known method, such as the method of U.S. Pat. No. 6,800,480. ECM of '480 patent was derived from feeder cells that have not been pre-treated with mitomycin C or gamma radiation. According to Example 3 of this invention, the ratio of undifferentiated HES cells maintained in an environment comprising ECM derived from HES cells pre-treated with mitomycin C and/or gamma ray radiation was about 78% after 5 passages, whereas the ratio of undifferentiated HES cells decreased to about 17% for cells that were maintained in an environment comprising ECM derived from feeder cells that had not been pre-treated with either mitomycin C or gamma ray radiation.

According to a preferred embodiment of this invention, HES cells, such as HES-3, H9, or TW1 cell lines, were plated onto culture dishes covered with ECM prepared as described above, and cultivated in the conditioned medium prepared as described above. Growth factors that promote cell growth or inhibit differentiation, e.g. fibroblast growth factor (FGF), leukemia inhibitory factor (LIF), stem cell factor (SCF), insulin-transferrin-selenium G supplement (ITS G supplement) may also be added into the conditioned medium during cultivation of HES cells (WO 03/020,920, U.S. 2003/0,017,589, U.S. Pat. No. 5,690,926, U.S. Pat. No. 5,453,357; Xu et al., Nat. Biotechnol., 19(10):971-974, 2001, and Richards, M. et. al., Nat Biotechnol., 20(9):933-936, 2002).

Determination of undifferentiated HES cells was done by following the morphological feature of the colonies, and furthered confirmed by the expression of biomarkers specifically expressed on the undifferentiated HES cells, such as alkaline phosphatase activity, Telomerase activity, octamer-binding transcription factor 4 (OCT-4), Nanog gene, and stage specific surface antigens such as SSEA-3, SEA-4, TRA-1-60 and TRA-1-81 (Thomason et al., Science 282(6):1145-1147, 1998; and Reubinoff et al., Nat. biotechnol. 18(4):399-404, 2000). Undifferentiated HES cells typically show high level of alkaline phosphatase activity, which can be detected by fixing the cells with suitable fixing agent, such as paraformaldehyde or ethanol and then developing with Vector Red as a substrate, as described by the manufacturer (Vector Laboratories, Burlingame, Calif.). As to telemerase acitivity, it was detected by commercial available telemerase acitivity assay kit. The expression of octamer-binding transcription factor 4 (OCT-4) and Nanog was detected by RT-PCR; and the expression of surface antigens such as SSEA-3, SEA-4, TRA-1-60 and TRA-1-81, were detected by immunohistochemical staining and/or by flow cytometry. The detection methods such as immunohistochemical staining, flow cytometry and RT-PCR are well know techniques in this art, and can be practiced by any one skilled in this art without undue experiments. In one example, at least 76% or 85% of the HES cells (i.e., TW1 cells) were positive stained for SSEA-4 when cultivated in either mECM or hECM, respectively. In another example, at least 91% or 90% of HES (i.e., H9 cells) were positive stained for SSEA-4 when cultivated in either mECM or hECM, respectively. In still another example, at least 89% or 86% of the HES cells (i.e., TW1 cells) were positive stained for biomarker, Oct-4, when cultivated in either mECM or hECM, respectively.

The HES cells of the invention may also be cryopreserved. The cells may be cryopreserved in a solution comprising, for example, dimethyl sulfoxide at a final concentration not exceeding 10%. The cells may also be cryopreserved in a solution comprising dimethyl sulfoxide and/or dextran. Other methods of cryopreserving cells are known in the art.

The HES cells of the invention may be used in the treatment of many kind of injury, disease and disability where tissues need to be replaced or regenerated. Some of these injury, disease and disability include but not limited to central nervous system (CNS) injuries, and the peripheral nervous system (PNS) injuries, such as Parkinson's and Alzheimer's diseases and other newodegenerative disorders, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer and other solid tumors, and AIDS.

The cells of the invention may also be co-administered with other agents, such as other cell types, growth factors, and antibiotics. Other agents may be determined by those of ordinary skill in the art.

Other than in the operating examples, or where otherwise indicated, all numbers expressing quantities of ingredients, reaction conditions, and so forth used in this application are to be understood as being modified in all instances by the term "about" Accordingly, unless the contrary is indicated, the numerical parameters set forth in this application are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It must be noted that as used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

All publications mentioned in this application are incorporated by reference to disclose and describe the methods and/or materials in connection with which the publications are cited. Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Methods, techniques, and/or protocols (collectively "methods") that can be used in the practice of the invention are not limited to the particular examples of these procedures cited throughout the specification but embrace any procedure known in the art for the same purpose. Furthermore, although some methods may be described in a particular context in the specification, their use in the instant invention is not limited to that context.

EXAMPLES

The following Examples are provided to illustrate certain aspects of the present invention and to aid those of skilled in the art in practicing this invention. These Examples are in no way to be considered to limit the scope of the invention in any manner.

Example 1

Culture of Human Embryonic Stem Cells 1.1 Preparation of Conditioned Medium

Conditioned medium for maintaining the culture of HES cell was prepared according to the following procedure. Briefly, primary mouse embryonic fibroblasts (PMEF) or human foreskin fibroblast (HFF, obtained from Animal Technology Research Institute, Taiwan) were plated in Dulbecco's Modified Eagle Medium (DMEM, obtained from Gibco Invitrogene) supplemented with 10% fetal bovine serum (FBS, obtained from HyClone). Cell cultures were maintained at 37° C. and 5% $CO_2$ and in a water-saturated atmosphere until they reached confluence, then 10 μg/ml mitomycin C was added to inactivate the fibroblasts. The inactivated fibroblasts were then re-grown in DMEM medium supplemented with 20% FBS, 1 mM β-mercaptoethanl (obtained from Gibco Invitrogene), 1% non-essential amino acids (obtained from Gibco Invitrogene), 1% glutamine (obtained from Gibco Invitrogene), and 1% insulin-transferring-selenium G supplement (ITS G supplement, obtained from Gibco Invitrogene) (See Richards, M. et al., Nat. Biotechnol., 20(9): 933-936, 2002). FBS may also be omitted an/or substituted by serum so as to obtain a serum-free growth medium. The medium in which the inactivated fibroblasts have been grown for at least 1 day was then collected for immediate use or stored at −80° C. for future usage. The medium thus collected was termed "conditioned medium". Based on the requirements of the cultured cells, the growth medium may contain other ingredients without limited to those discussed herein.

1.2 Preparation of Extracellular Matrix (ECM)

Extracellular matrix for maintaining HES cells was prepared according to the following procedure. Briefly, primary mouse embryonic fibroblasts (PMEF) or human forskin fibroblasts (HFF) (obtained from Animal Technology Research Institute, Taiwan) were grown in DMEM medium supplemented with 10% FBS. When the cells reached 90% confluence, 10 μg/ml mitomycin C was then added to inactivate the fibroblasts. These inactivated cells were trypsinized, counted, re-plated in the culture dish, and confluence cultured for at least 2 days, then were lysed with 0.05N NaOH or 0.1% trinitrotoluene (obtained from Sigma) for a period of 1-15 min and rinsed with Phosphate Buffered Saline (pH 7.4) (1×, obtained from Gibco Invitrogene) to remove organelles and nucleus. The extracellular matrix of PMEF or HFF thus prepared can be used fresh or stored away for future use in PBS at 4° C. for at least 9 months.

Figure 1B:
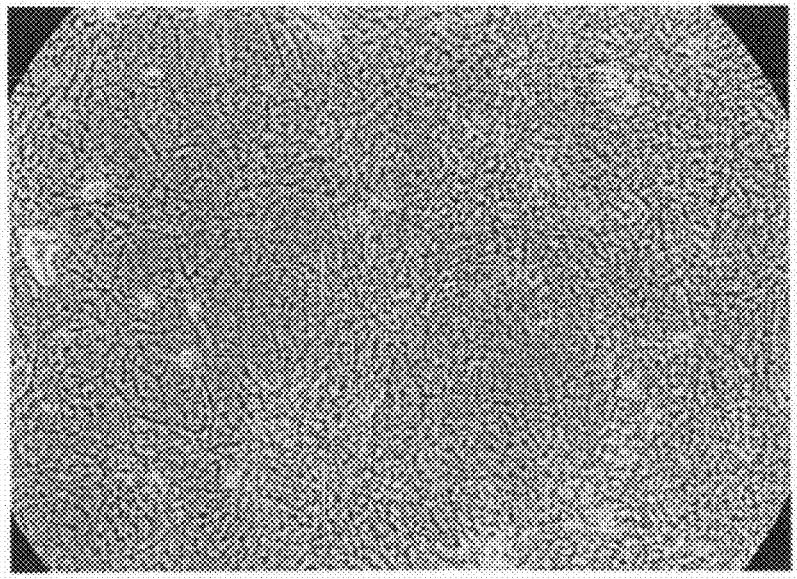
Figure 1C:
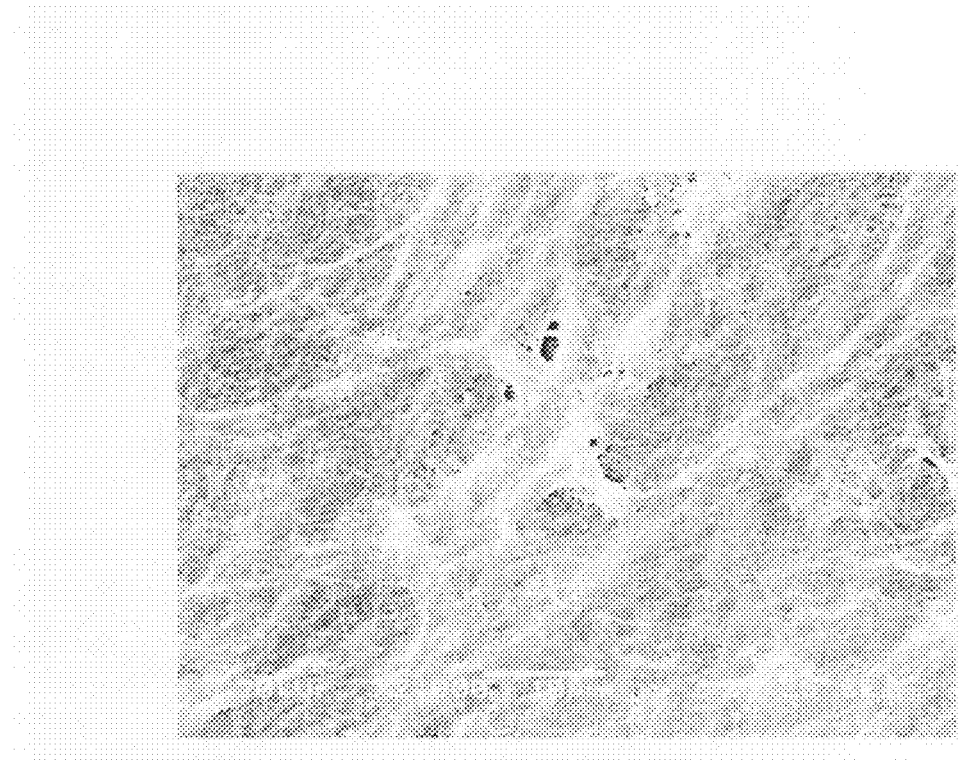
FIG. 1C is a scanning electron microscope (2,000×) photograph of the macrofibril bundles and network structure of the ECM derived from PMEF.
Figure 2A:
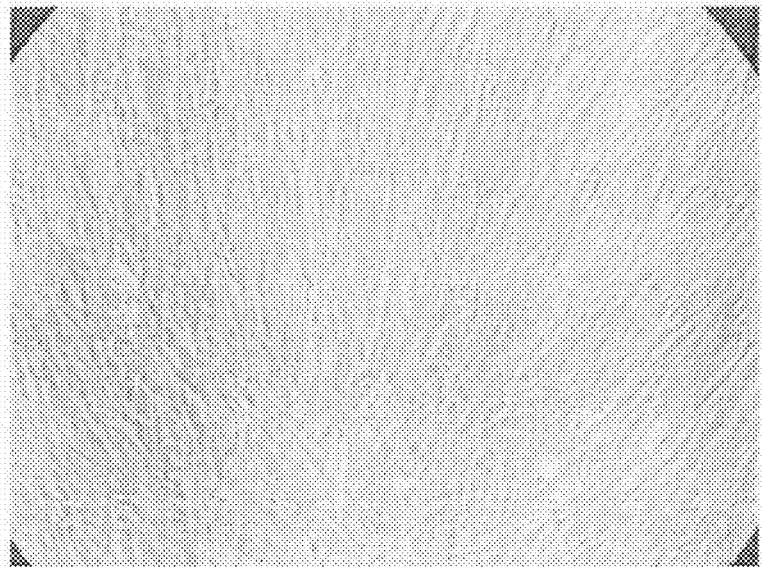
FIGS. 2A and 2B are phase-contrast photographs of ECM derived either from PMEF or human foreskin fibroblast (HFF), respectively, when viewed under a light transmitted microscope (300×)
Figure 2B:
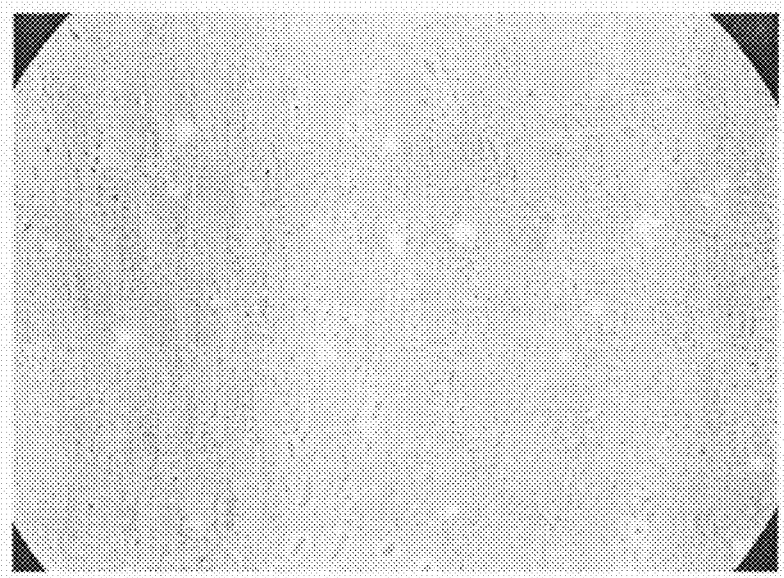

FIG. 1 illustrated the morphology of the primary culture of PMEF (FIG. 1A) and the ECM derived from PMEF (FIG. 1B) viewed by a light transmitted microscope. FIG. 1C illustrated the macrofibril bundles and network structure of said ECM of FIG. 1B viewed by a scanning electron microscope. The morphology of HFF cells and the structure of ECM derived from HFF are illustrated in FIG. 2A and FIG. 2B, respectively.

1.3 Culturing of HES Cells

HES cells including HES-3 (ESI cell international), H9 (WiCell Research Institute, Inc) or TW1 (Industrial Technology Research Institute, Taiwan) cell lines, were counted and plated onto culture dishes covered with the ECM of Example 1.2 and incubated with the conditioned medium of Example 1.1. Culture medium was replaced every 1-2 days and cell cultures were maintained at 37° C. and 5% $CO_2$ and in a water-saturated atmosphere for 6-8 days. The HES cells were passaged by mechanical dissection or enzyme digestion. HES cells may continue to grow for at least 5 passages and remain substantially undifferentiated.

Figure 3A:
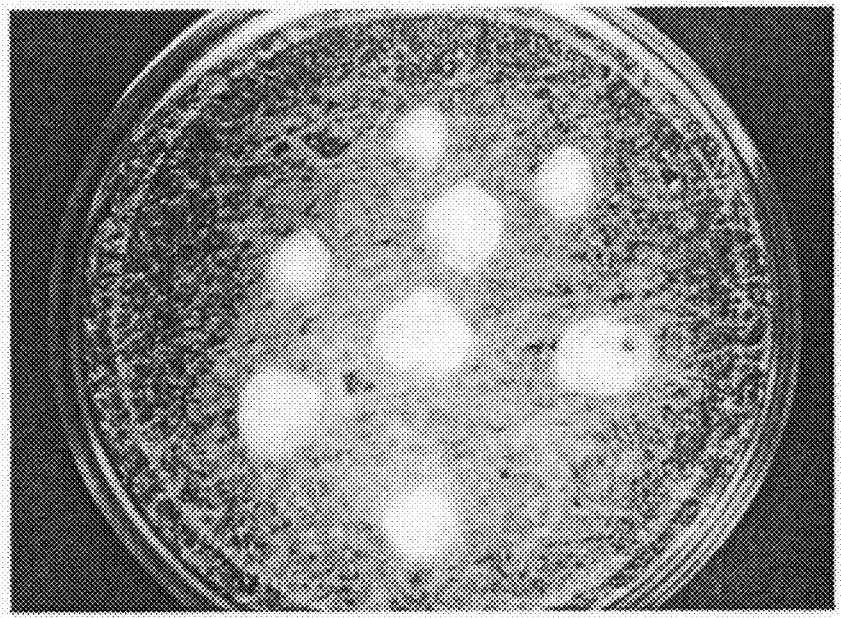
FIG. 3 are photographs of HES-3 cells maintained in cultured dishes covered with mouse feeder cells (FIG. 3A) or with ECM derived either from PMEF (mECM) (FIG. 3B) or from HFF (hECM) (FIG. 3C)
Figure 3B:
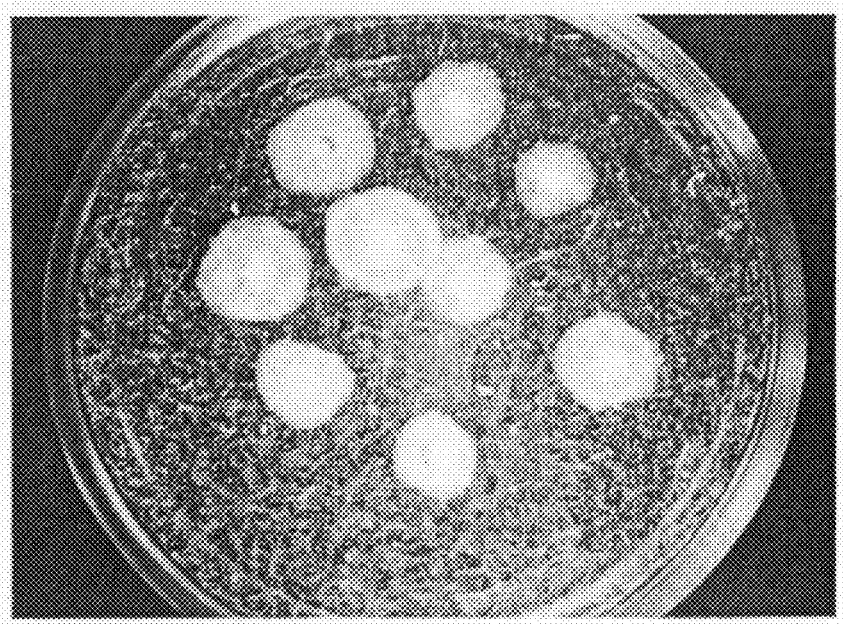
Figure 3C:
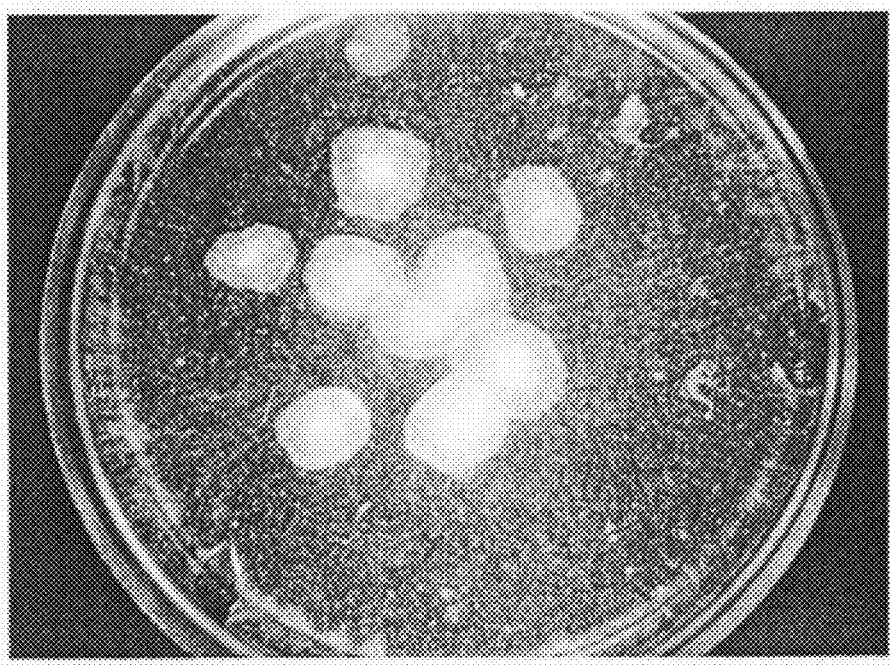

FIG. 3 illustrates the morphologies of undifferentiated HES-3 colonies grown on mouse feeder cells or on ECM derived from fibroblasts in the presence of the conditioned medium as described above. The percentage of undifferentiated HES colonies is 80% for HES-3 cells grown on mouse feeder cells (FIG. 3A), and is 100% for HES-3 cells grown on ECM derived from either PMEF (mECM) (FIG. 3B) or HFF (hECM) (FIG. 3C).

Example 2

Phenotypic Characterization of HES Cells of Example 1.3

2.1 Undifferentiation of HES Cells of Example 1.3 Characterized by the Expression of Bio-Markers The HES cells obtained in Example 1.3 were analyzed for bio-markers specifically expressed in HES cells to determine the undifferentiated level of HES cells. The bio-markers thus analyzed included alkaline phosphatase; stage-specific embryonic antigen such as SSEA-3, SSEA-4, TRA-1-60, and TRA-1-81; octamer-binding transcription factor 4 (OCT-4); Nanog gene expression, and Telomerase activity. The assayed methods were those described by Richards, M. et al., (Nat Biotechnol., 20(9):933-936, 2002); Xu et al (Nat. Biotechnol., 19(10):971-974, 2001); Thomson J. A. etal., (Science, 282(6):1145-1147, 1998); and Reubinoff B. E. et al., (Nat Biotechnol. 18(4):399-404, 2000).

Figure 4A:
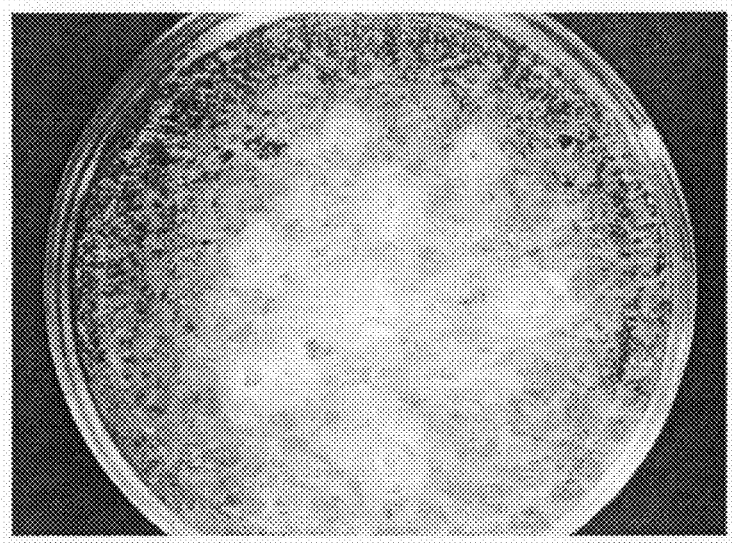
FIG. 4 are photographs of the alkaline phosphatase activity of HES-3 cells maintained in culture dishes covered with mouse feeder cells (FIG. 4A) or with mECM (FIG. 4B) or hECM (FIG. 4C) according to one embodiment of this invention.
Figure 4B:
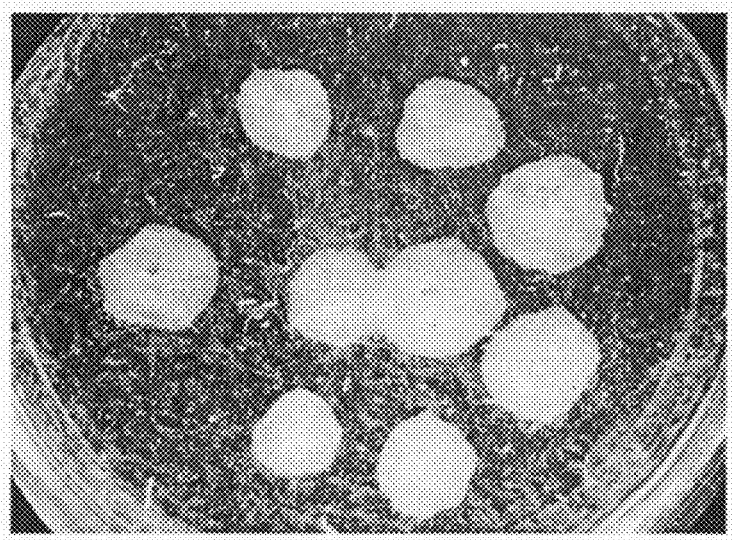
Figure 4C:
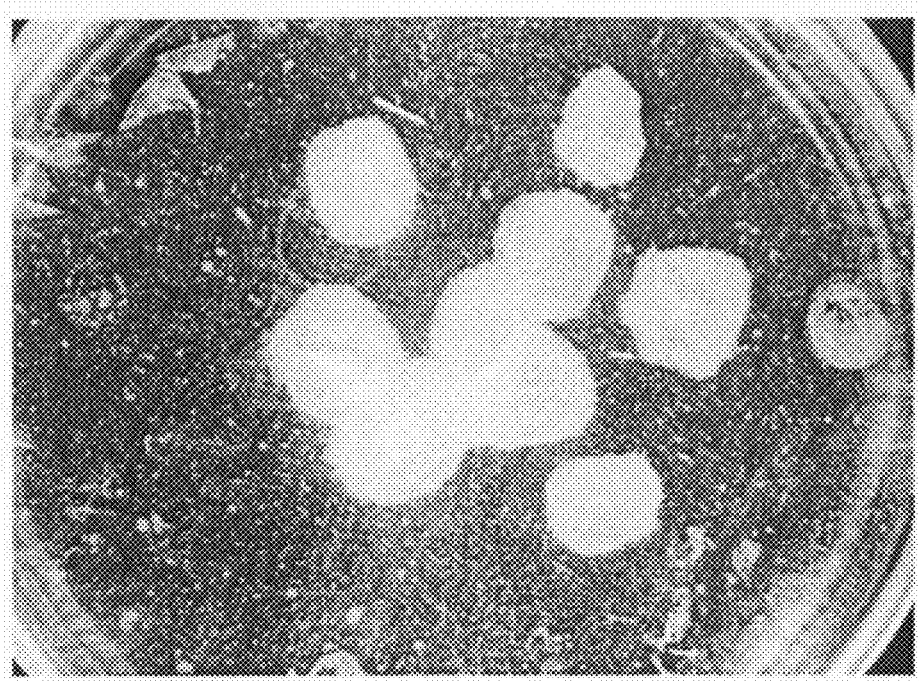

The alkaline phosphatase activity was assayed according to the manufacture's instruction provided in the assay kit (obtained from Vector Laboratories, Inc.) and the staining result illustrated in FIG. 4 indicated that the undifferentiation percentage is 80% for HES-3 cells maintained on the mouse feeder cells (FIG. 4A); and is 100% for cells grown on ECM derived from either PMEF (FIG. 4B) or HFF (FIG. 4C), respectively. The HES cells may be continuously sub-cultured for at least five passages with differentiation percentage of the culture system of the present invention remain less than about 20%.

Figure 5:
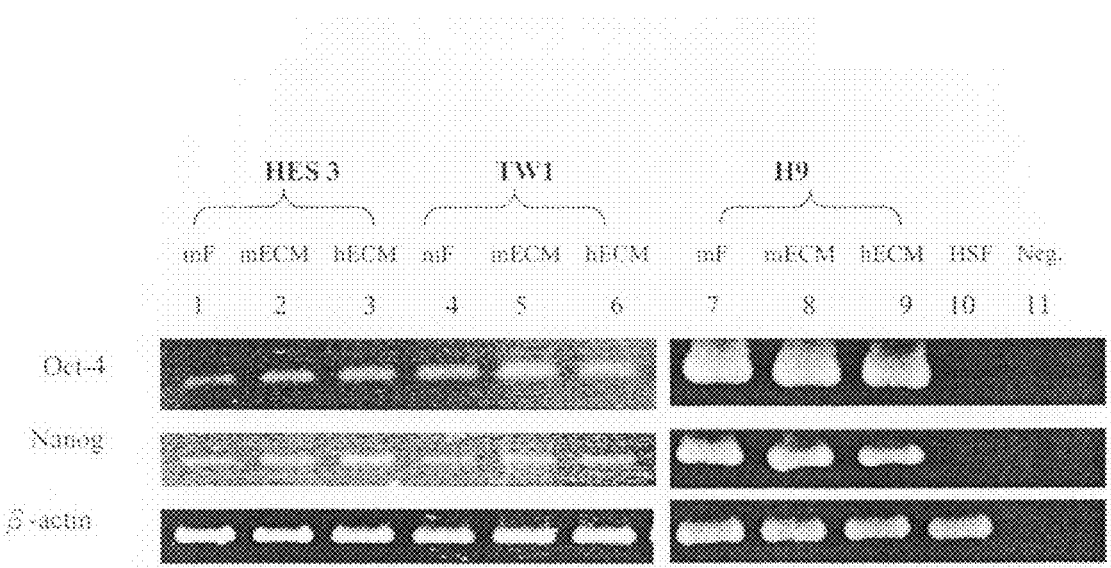
FIG. 5 illustrates the expression of OCT-4 and Nanog on HES cells of Example 1.3, in which PMEF (lanes 1, 4 and 7), HSF (lane 10), and mECM (lanes 2, 5 and 8) or hECM (lanes 3, 6 and 9) are used as a feeder layer or matrix during culture; and lane 11 is a negative control that was run without cells.

Both the expression of OCT-4 and Nanog were assayed by RT-PCR and results were illustrated in FIG. 5. Using a RT-PCR analysis, it was found that HES cells including HES-3, TW1 and H9 cells maintained in the feeder-free system of this invention (i.e., a system containing both ECM of Example 1.2 and conditioned medium of Example 1.1) expressed similar amounts of transcription factors of OCT-4 (FIG. 5, Oct-4 band: lanes 2, 3, 5, 6, 8 and 9) and Nanog (FIG. 5, Nanog band: lanes lanes 2, 3, 5, 6, 8 and 9) as that of the control cells that grown on mouse feeders (FIG. 5, both Oct-4 and Nanog bands: lanes 1, 4 and 7), indicating that the feeder-free culture system of this invention is capable of maintaining the undifferentiated growth of HES cells.

Figure 6A:
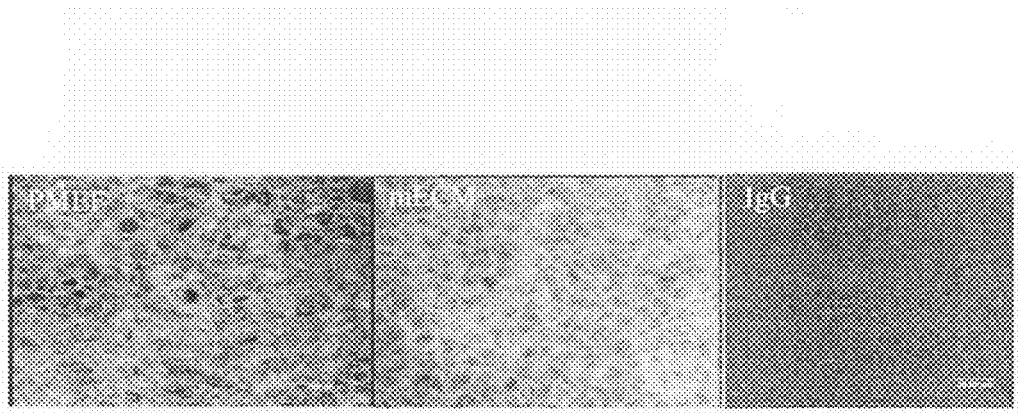
FIG. 6 illustrates the expression of surface markers of SSEA-4 (FIG. 6A), and TRA-1-60 (FIG. 6B) detected by immunohistochemistry for HES cells grown on PMEF feeder, hECM or on mECM prepared according to one embodiment of this invention.
Figure 6B:
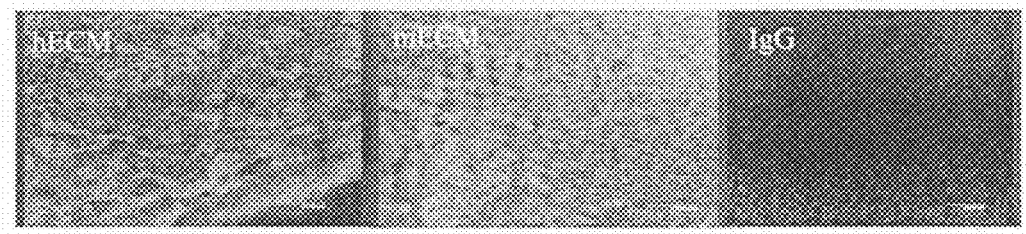

The undifferentiated HES cells were also characterized in expressing stage specific surface markers such as SSEA-4 and TRA-1-60, which were detected by immunohistochemistry and results were illustrated in FIG. 6. Staining intensity for SSEA-4 (FIG. 6A) and TRA-1-60 (FIG. 6B) were both strong for HES cells either grown on feeder cells or on ECM prepared from said feeder cells according to the procedures described above.

Table 1 provided a quantified comparison of the cell markers expressed on HES cells. HES cells were maintained on mouse feeders (i.e., PMEF) or on ECM isolated from either mouse (mECM) or human fibroblasts (hECM), and cell markers such as SSEA-4 and Oct-4 were detected by flow cytometry. It was found that the amount of cell markers expressed on both TW1 and H9 cells that were maintained in the feeder-free system of this invention were comparable to that on cells maintained in the conventional system comprised of feeder layers of PMEF. Results from Table 1 were consistent with the findings of FIG. 5, that the feeder-free system of this invention was at least as effective as the conventional feeder system in supporting and/or maintaining the undifferentiated growth of HES cells.

TABLE 1

| HES cells | % of Staining of SSEA-4 | | | % of Staining of Oct-4 | | |
| --- | --- | --- | --- | --- | --- | --- |
| | PMEM | mECM | hECM | PMEM | mECM | hECM |
| TW1 | 84%[1] | 76%[1] | 85%[1] | 89%[2] | 89%[2] | 86%[2] |
| H9 | 93%[3] | 91%[3] | 90%[3] | — | — | — |

[1]TW1 cells were cultured in PMEF feeder layers for 19 passages, then continued to culture in PMEF, mECM or hECM for another 8 passages.
[2]TW1 cells were cultured in PMEF feeder layers for 19 passages, then continued to culture in PMEF, mECM or hECM for another 26 passages.
[3]H9 cells were cultured in PMEF feeder layers for 33 passages, then continued to culture in PMEF, mECM or hECM for another 8 passages.

Figure 7:
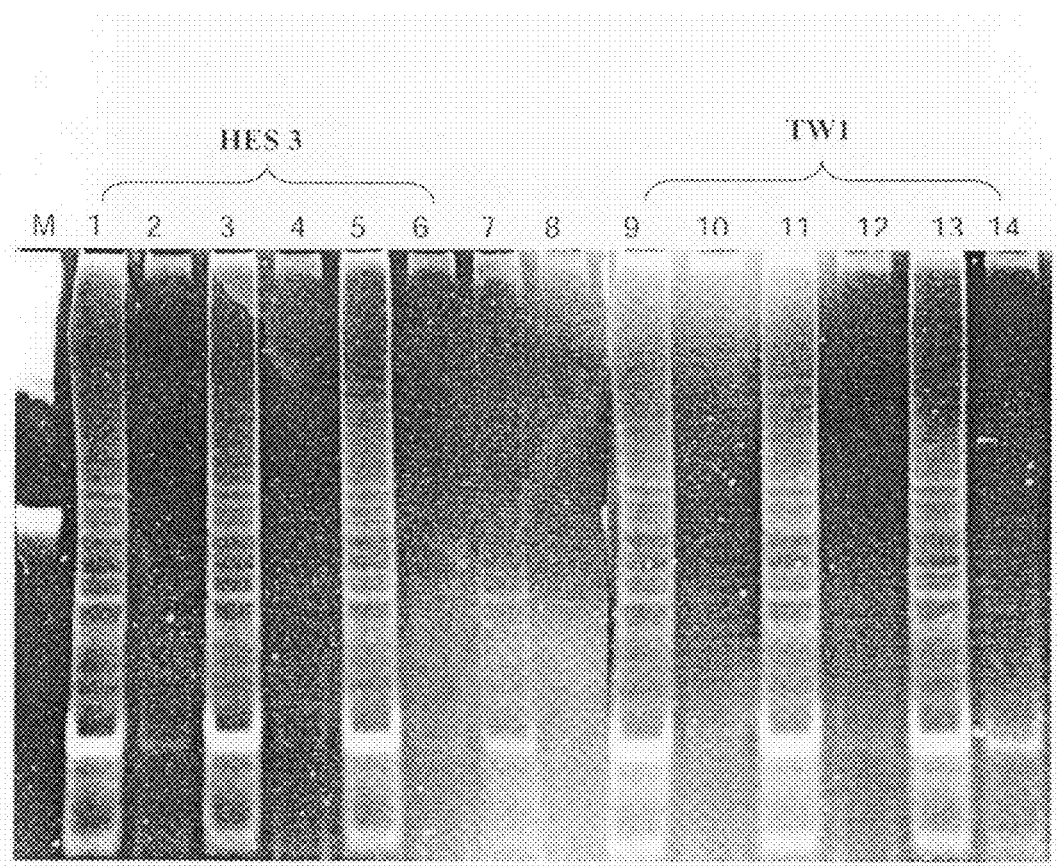
FIG. 7 illustrates the telomerase activity of HES cells grown on PMEF feeder (lane 1, 9), or on mECM (lane h3, 11) or hECM (lane 5, 13) prepared according to one embodiment of this invention; the telomerase-expressing tumor line HeLa was used as a positive control (lane 7), and the heat-inactivated total cellular protein was used as the negative control (lanes 2, 4, 6, 8, 10, 12, and 14)

In contrast to somatic cells, whose telomeres usually shorten with age, germ lines and embryonic tissues express high level of telomerase activity so that telomere repeats are added to chromosome ends to maintain the telomere length as an indication of the immortality of the germ lines and embryonic tissues. FIG. 7 illustrated the telomerase activity of HES cells maintained in either conventional feeder system or the feeder-free system of this invention. It was found that both HES-3 and TW1 cell lines, cultured on either conventional PMEF feeder cells (FIG. 7, lanes 1 and 9) or on ECM isolated form mitomycin C inactivated-mouse fibroblasts (mECM) (FIG. 7, lanes 3 and 11) or human fibroblasts (hECM) (FIG. 7, lanes 5 and 13) expressed strong of telomerase activity, wherease the heat inactivated cellular proteins had no detectable telomerase activity (FIG. 7, lanes 2, 4, 6, 8, 10, 12 and 14). The telomerase-expressing tumor cell lines HeLa was used as a positive control (FIG. 7, lane 7). This result confirmed that the feeder-free system of this invention was as effective as the conventional feeder system in supporting the undifferentiated growth of HES cells.

Figure 8A:
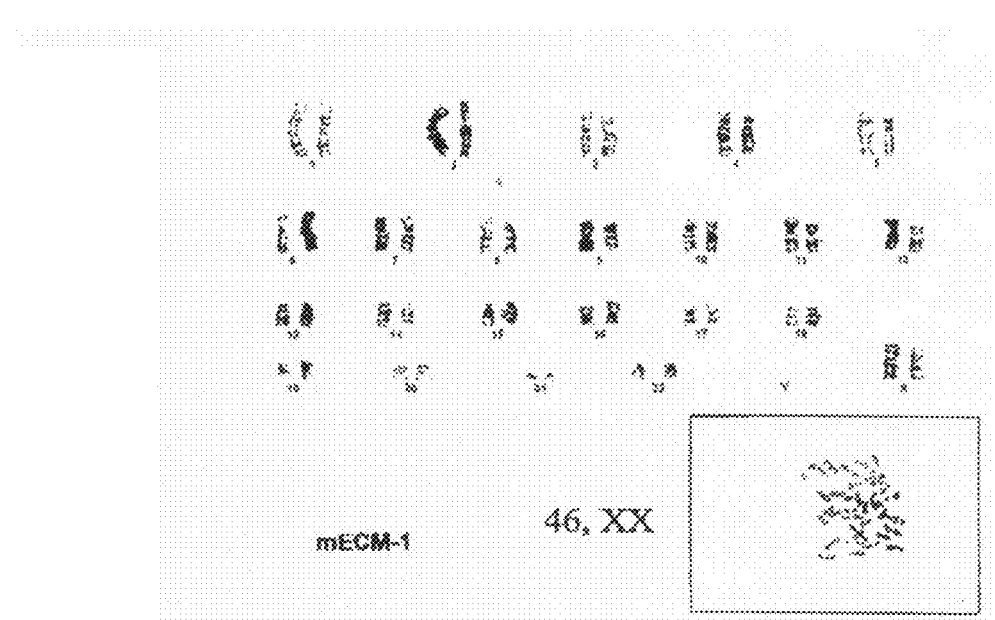
FIG. 8 illustrates the karyotype analysis of HES cells grown on mECM (FIG. 8A) or hECM (FIG. 8B) prepared according to one embodiment of this invention.
Figure 8B:
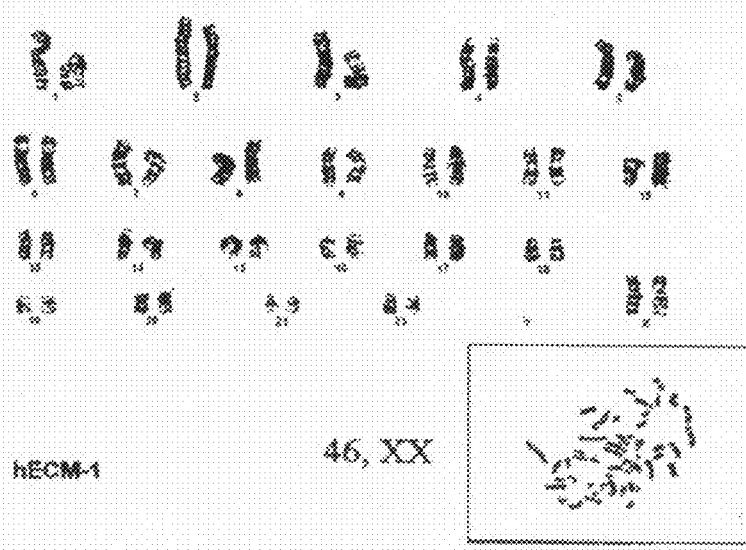

Moreover, it was further confirmed that HES cells such as TW1 cell lines cultured on ECM isolated form mitomycin C inactivated-mouse fibroblasts (mECM) (FIG. 8A) or human fibroblasts (hECM) (FIG. 8B) had a normal karyotype 46, XX karyotype after continuous culture of 10 passages.

Figure 9:
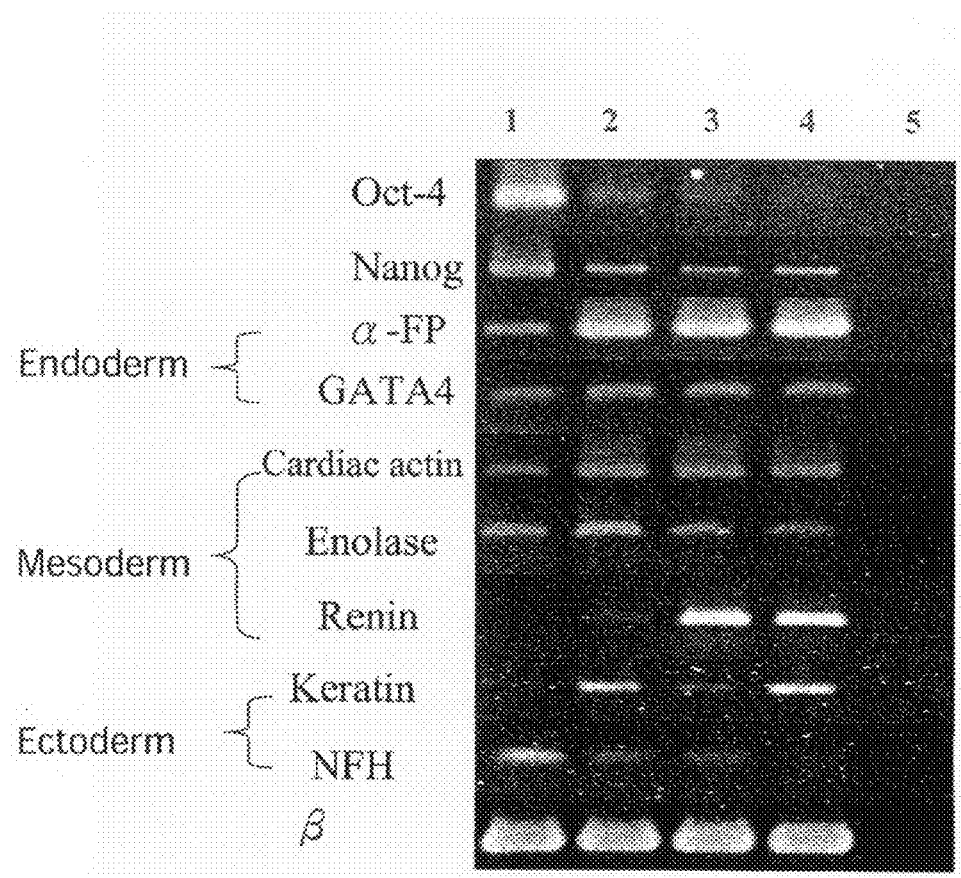
FIG. 9 illustrates the expression of cell genes of embryoid bodies derived from HES cells grown on PMEF feeders (lane 2), mECM (lane 3) or hECM (lane 4); the expression of genes was detected by RT-PCR, and undifferentiated HES cells grown on PMEF was used as a control (lane 1), whereas the reaction mixture without RNA was used as a negative control (lane 5)
Figure 10:
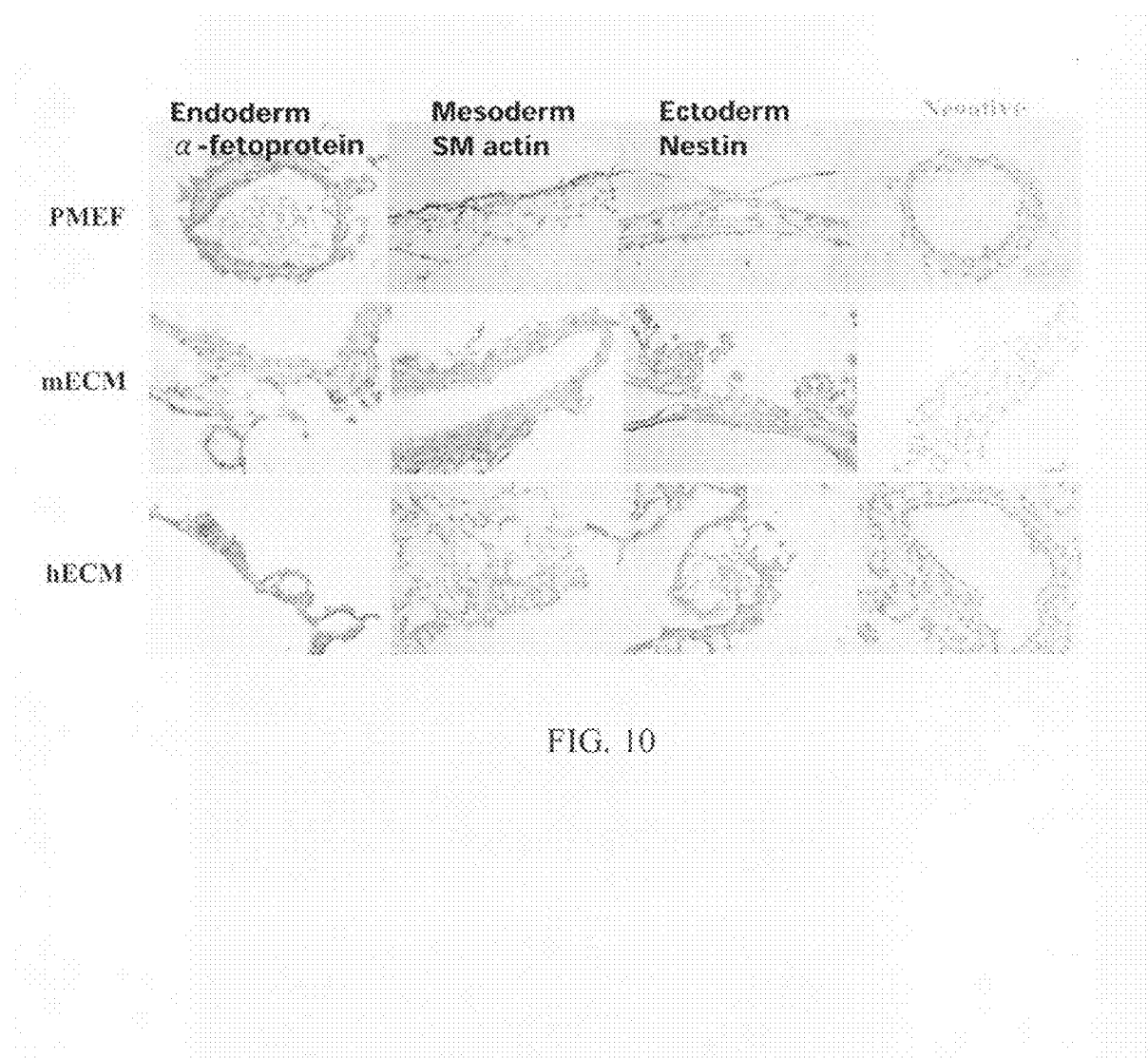
FIG. 10 illustrated the immunohistochmical analysis of the expressed proteins originated from each of three germ layers of embryonic bodies (at day 30) derived from the HES cells maintain on PMEF feeder, mECM or hECM, respectively; the isotype normal antibody was used as the negative control.
Figure 11A:
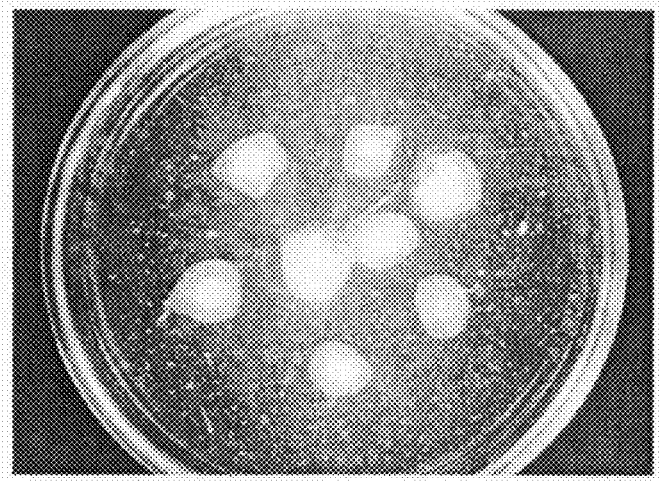
FIGS. 11A and 11C are phase-contrast photographs of the HES cells maintained in culture dishes covered with hECM pre-inactivated by mitomycin C (FIG. 11A) or with hECM without mitomycin C pre-inactivation (FIG. 11C) according to one embodiment of this invention.
Figure 11B:
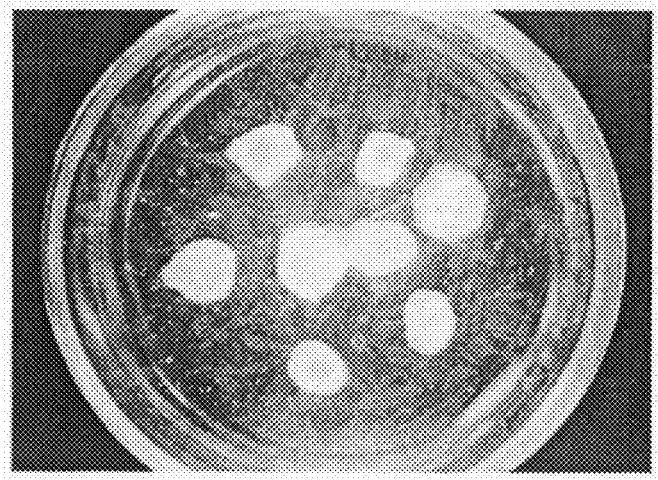
FIGS. 11B and 11D are photographs of the alkaline phosphatase activity of HES cells of FIGS. 11A and 11C, respectively.
Figure 11C:
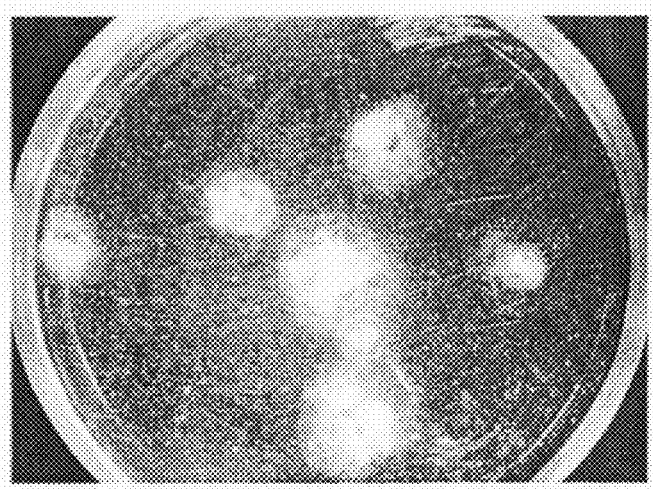
Figure 11D:
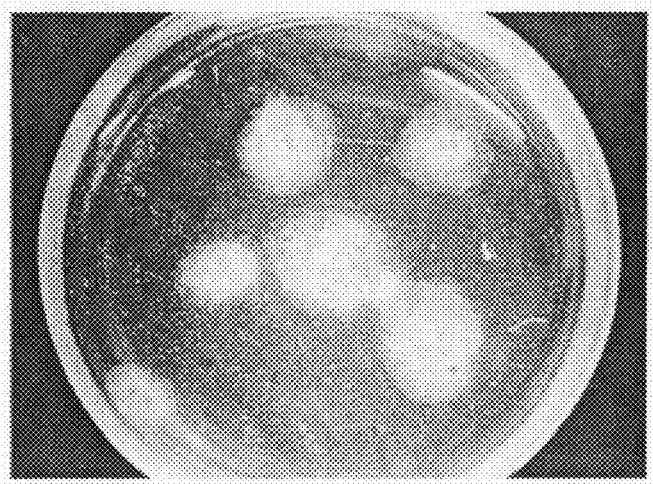

2.2 Differentiation of HES Cells of Example 1.3 Characterized by the Expression of Cell Genes or Proteins of Each of the Three Germ Layers This example illustrated the differentiating capability (i.e., puripotency) of the HES cells cultured in the feeder-free system of this invention. Puripotency of the undifferentiated HES cells cultured according to the procedure described in Example 1.3 was determined by formation of embryoid bodies (EBs) in suspension culture environment, and further confirmed by the detection of the expressed cell genes (FIG. 9) or proteins (FIG. 10) originated from each of the three germ layers. Total RNA of embryoid bodies at 10 days were analyzed for genes originated from endoderm (such as genes of α-fetoprotein (α-FP) and GATA4), mesoderm (such as genes of cardiac actine, enolase) and ectoderm (such as genes of keratin and neuro filament heavy protein (NFH)) by use of reverse transcription polymerase chain reaction (RT-PCR). Results were illustrated in FIG. 9. Expression of cell genes such as α-FP, GATA4, cardiac actine, enolase and NFH of embryoid bodies derived from the HES cells cultured in mECM or hECM (FIG. 9, lanes 3 and 4, respectively) are comparable to those of embryoid bodies derived from the HES cells cultured in the presence of PMEF feeder cells (FIG. 9, lane 2). Expression of proteins in 30 days EBs corresponding to genes such as α-FP of endoderm, actin of mesoderm and nestin of ectoderm were provided in FIG. 10.

Example 3

Unique Characteristics of the ECM of Example 1.2 in Maintaining the Undifferentiated Growth of HES Cells It is unexpectedly discovered that the ECM prepared by this invention is unique in maintaining the undifferentiated growth of HES cells, when compared with ECM prepared by other method, i.e., ECM prepared from feeder cells that were confluent but were not pre-treated with 10 μg/ml of mitomycin C. Results were illustrated in FIG. 11

HES cells that were maintained in a culture dish covered with ECM of Example 1.2 showed strong alkaline phosphatase activity (FIG. 11B) with 78% of HES cells remained undifferentiated after 5 passages, compared with HES cells that were grown in ECM prepared from feeder cells without pre-inactivation by either mitomycin C or gamma ray radiation (FIG. 11D), in which merely 17% of HES cells remained undifferentiated. The morphology of HES cells maintained in either condition before staining of Alkaline phosphatase activity were illustrated in FIGS. 11A and 11C, respectively.

INDUSTRIAL APPLICABILITY

The culture system for HES cells presented herein offers the following advantages: (1) It prevents the potential risks of transmitting any pathogen from the animal/human feeder cells to HES cells, particularly when the current system of propagating human/animal co-culture is construed for the purpose of cell therapy; (2) A better quality control of HES cells (i.e., remained substantially undifferentiated) can be reached; (3) A mass/bulk production of HES cells is feasible; and (4) It sheds light on future clinical application of HES cells.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A composition for maintaining the undifferentiated growth of human embryonic stem cells, the composition comprising:

a substrate covered with an extracellular matrix isolated from inactivated feeder cells;

a conditioned medium having been preconditioned by inactivated feeder cells; and undifferentiated human embryonic stem cells;

wherein the feeder cells are selected from the group consisting of human foreskin fibroblasts and primary mouse embryonic fibroblasts and wherein the feeder cells have been inactivated by treatment with 10μg/mL mitomycin C.

* * * * *